United States Patent
Jeong et al.

(10) Patent No.: US 12,295,804 B2
(45) Date of Patent: May 13, 2025

(54) PATCH ATTACHABLE TO TEETH

(71) Applicant: LG HOUSEHOLD & HEALTH CARE LTD., Seoul (KR)

(72) Inventors: Yong-Beom Jeong, Seoul (KR); Seong-Eun Bang, Seoul (KR); Jae-Hyun Ahn, Seoul (KR); So-Ra Choi, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 168 days.

(21) Appl. No.: 17/787,132

(22) PCT Filed: Dec. 18, 2020

(86) PCT No.: PCT/KR2020/018711
§ 371 (c)(1),
(2) Date: Jun. 17, 2022

(87) PCT Pub. No.: WO2021/125894
PCT Pub. Date: Jun. 24, 2021

(65) Prior Publication Data
US 2023/0027167 A1    Jan. 26, 2023

(30) Foreign Application Priority Data

Dec. 19, 2019  (KR) .......................... 10-2019-0170801
Dec. 17, 2020  (KR) .......................... 10-2020-0177268

(51) Int. Cl.
*A61C 19/06*    (2006.01)
(52) U.S. Cl.
CPC .................................. *A61C 19/063* (2013.01)
(58) Field of Classification Search
CPC .................................................... A61C 19/063
See application file for complete search history.

(56) References Cited

U.S. PATENT DOCUMENTS

| | | | | |
|---|---|---|---|---|
| 2,633,637 A | * | 4/1953 | Lucia | A61C 9/00 433/70 |
| 4,547,155 A | * | 10/1985 | Adler | A61C 19/05 433/70 |
| 5,914,118 A | | 6/1999 | Yamamura et al. | |
| 5,989,569 A | * | 11/1999 | Dirksing | A61C 19/066 106/35 |

(Continued)

FOREIGN PATENT DOCUMENTS

| CN | 102626379 A | 8/2012 |
|---|---|---|
| CN | 102631292 A | 8/2012 |

(Continued)

OTHER PUBLICATIONS

Dentaltix (Dental Supplies Distributor )[online]. [retrieved Mar. 28, 2024]. Retrieved from the Internet: https://www.dentaltix.com/en/blog/ultimate-guide-dental-waxes#:~:text=It%20is%20essentially%20composed%20of,2.5% (Year: 2023).*

(Continued)

*Primary Examiner* — Cris L. Rodriguez
*Assistant Examiner* — Luis Ruiz Martin
(74) *Attorney, Agent, or Firm* — Birch, Stewart, Kolasch & Birch, LLP

(57) ABSTRACT

The present disclosure provides a patch attachable to the occlusal plane of posterior teeth, which includes: a drug layer; a backing layer in contact with the drug layer; and a removable part in contact with the backing layer. The patch can be provided as a single-sided type or a double-sided type. It may also be provided as a linear type or a symmetric type. The present disclosure is directed to providing a patch that can be easily attached to the occlusal plane of posterior teeth.

13 Claims, 15 Drawing Sheets

(56) References Cited

U.S. PATENT DOCUMENTS

| | | | | |
|---|---|---|---|---|
| RE42,126 E | * | 2/2011 | Ye | A61K 8/37 |
| | | | | 424/443 |
| 8,986,005 B2 | * | 3/2015 | Montgomery | A61C 19/066 |
| | | | | 433/80 |
| 10,603,252 B2 | | 3/2020 | Kim et al. | |
| 2002/0006387 A1 | * | 1/2002 | Sagel | A61Q 11/00 |
| | | | | 424/53 |
| 2002/0081555 A1 | * | 6/2002 | Wiesel | A61C 19/063 |
| | | | | 433/80 |
| 2005/0260544 A1 | * | 11/2005 | Jones | A61C 19/063 |
| | | | | 424/49 |
| 2005/0276760 A1 | * | 12/2005 | Lokken | A61K 8/0208 |
| | | | | 424/53 |
| 2008/0131845 A1 | | 8/2008 | Viscomi | |
| 2020/0390676 A1 | * | 12/2020 | Strand | A61K 8/8147 |

FOREIGN PATENT DOCUMENTS

| | | |
|---|---|---|
| CN | 103585027 A | 2/2014 |
| CN | 108289860 A | 7/2018 |
| JP | 57-103640 A | 6/1982 |
| JP | 09-235220 A | 9/1997 |
| JP | 2003-113092 A | 4/2003 |
| JP | 2004-538085 A | 12/2004 |
| JP | 2007-501092 A | 1/2007 |
| KR | 10-2005-0119914 A | 12/2005 |
| KR | 20-0471737 Y1 | 3/2014 |
| KR | 20170040888 A * | 4/2017 |
| KR | 10-1924289 B1 | 11/2018 |
| WO | WO 03/015656 A2 | 2/2003 |
| WO | WO 2004/105628 A2 | 12/2004 |
| WO | WO 2009/150712 A | 12/2009 |
| WO | WO 2017/043800 A1 | 3/2017 |

OTHER PUBLICATIONS

International Search Report for PCT/KR2020/018711 mailed on Mar. 26, 2021.

* cited by examiner (a)                    (b)

[ A ]

[ A ]

[ B ]

[ A ]  [ B ]

PATCH ATTACHABLE TO TEETH

TECHNICAL FIELD

The present application claims priority to Korean Patent Application No. 10-2019-0170801 filed on Dec. 19, 2019 and Korean Patent Application No. 10-2020-0177268 filed on Dec. 17, 2020 in the Republic of Korea, the disclosures of which are incorporated herein by reference. The present disclosure relates to an oral patch, more specifically to a tooth-attachable patch for attaching on the surface of teeth.

BACKGROUND ART

Teeth can be largely classified into anterior teeth including 1) incisors and 2) canines and posterior teeth including 3) premolars and 4) molars. In the industry, patches that are attached inside the mouth to conveniently deliver drugs (for example, ingredients for whitening teeth, preventing or improving periodontal diseases, etc.) to or around the teeth are being researched. The existing oral patch products can be easily attached to flat surfaces such as anterior teeth or labial surface, but they are not suitable to be uniformly attached to the uneven occlusal plane of posterior teeth for chewing food. In addition, because the occlusal plane of molars is located deep in the mouth, fingers or special devices should be used to attach the patch on the occlusal plane and it is difficult to attach it.

In addition, the existing gel- or paste-type products have the problems that, although they can be coated on the occlusal plane unlike the patch-type products, special devices have to be used and it is not easy to maintain sufficient time for drug delivery after the coating.

Meanwhile, the tooth-attachable patch has the problem that, when it is attached to or removed from the surface of teeth, the drug may adhere to fingers and the fingers may touch the surface of teeth or gums. The present disclosure has been devised to solve these problems and improve the structure of the patch.

DISCLOSURE

Technical Problem

The present disclosure is directed to providing a patch that can be attached to the occlusal plane of posterior teeth and used conveniently. The present disclosure is also directed to providing a patch that can be attached to the occlusal plane of posterior teeth and can be removed easily by brushing.

The present disclosure is also directed to providing a new type of tooth-attachable patch with a handle part provided to the patch attached on the surface of teeth.

Technical Solution

The present disclosure provides a patch that can be easily attached to the occlusal plane of posterior teeth.

The patch may comprise a removable part 11, 21 and a remaining part 12, 22. The removable part may be a handle layer and may be removed after the remaining part is attached to posterior teeth. In an exemplary embodiment, the remaining part may comprise or consist of: (1) a drug layer; and (2) a backing layer in contact with the drug layer. In another exemplary embodiment, the remaining part may further include a wax layer.

The patch may be a linear type 1 that can be provided to one side of left and right teeth, or may be a symmetric type 2 that can be provided to both sides at the same time. FIG. 1 schematically shows a linear-type patch 1 seen from above. The linear-type patch 1 has a remaining part 12 formed on a removable part 11. FIG. 2 and FIG. 3 schematically show an example of symmetric-type patches 2 seen from above. FIG. 2 shows an example of a patch having a U-shaped removable part, and FIG. 3 shows an example of a patch having a V-shaped removable part. The remaining parts of the symmetric-type patches 2 shown in FIGS. 2 and 3 can be attached to left and right teeth at the same time because the remaining parts are located at both ends.

Hereunder is given a more detailed description.

In an exemplary embodiment, the present disclosure provides a single-sided type patch attachable to the occlusal plane of posterior teeth. It is schematically shown in FIG. 4. Specifically, an exemplary embodiment of the single-sided type patch attachable to the occlusal plane of posterior teeth is described referring to FIG. 4. The patch may sequentially have a (1) drug layer 122; (2) a backing layer 121 in contact with the drug layer; and (3) a handle layer 11 (removable part) in contact with the backing layer. The drug layer and the backing layer may constitute a remaining part, and the handle layer may constitute a removable part. The patch may consist of or include the remaining part and the removable part. In an exemplary embodiment, when the patch is pressed with upper and lower posterior teeth, the drug layer is attached to the occlusal plane of one or more of upper posterior teeth and lower posterior teeth. Specifically, the drug layer has tackiness on one side because it has to be attached to the occlusal plane of posterior teeth.

In an exemplary embodiment, the present disclosure provides a double-sided type patch attachable to the occlusal plane of posterior teeth. It is schematically shown in FIG. 5. Specifically, an exemplary embodiment of the double-sided type patch attachable to the occlusal plane of posterior teeth is described referring to FIG. 5. The patch may sequentially have a (1) drug layer 122; (2) a backing layer 121; (3) a handle layer 11 (removable part); a (2)-1 backing layer 121; and a (1)-1 drug layer 122. When the patch is pressed with upper and lower posterior teeth, the drug layer may be attached to the occlusal plane of upper posterior teeth and lower posterior teeth at the same time. Specifically, the patch may have a structure wherein the backing layer and the drug layer are disposed sequentially on the back side of the removable part so that the drug layer can be attached to the occlusal plane of upper posterior teeth and lower posterior teeth at once. The handle layer may also be expressed as a removable part.

In an exemplary embodiment of the present disclosure, the removable part of the patch attachable to the occlusal plane of posterior teeth may have an area at least larger than that of the backing layer and the drug layer, and may have a protruding handle. Specifically, the drug layer and the backing layer included in the patch of the present disclosure may have the same length×breadth sizes, and the size may be about 1 cm×4 cm. The handle may have any shape which allows easy attachment and removal of the patch to and from the occlusal plane of posterior teeth. For example, the removable part may be prepared to be longer in length or breadth than the drug layer and the backing layer of the single-sided type or the double-sided type patch to form a handle. The inventors of the present disclosure have designed a symmetric-type patch structure as a result of striving for a shape that can be conveniently attached to left and right teeth. In an exemplary embodiment, the patch attachable to the occlusal plane of posterior teeth may be a symmetric-type patch having one removable part with a protruding handle formed and two remaining parts formed at both ends of the removable part. Each of the both ends of the symmetric-type patch may be equipped with a backing layer in contact with the removable part; and a drug layer in contact with the backing layer. In the present specification, the symmetric-type patch means that the same layer may exist at both ends of the removable part, and should not be construed as a limiting meaning that the shape or content of the layer at both ends should be the same. For example, a protruding U-shaped convex portion (or V-shaped sharp portion) becomes the removable part. A patch according to another exemplary embodiment may have a removable part protruding from the U-shaped convex portion, and the backing layer and the drug layer may be formed sequentially on the removable part at both ends of the U-shaped portion. A patch according to another exemplary embodiment may have a removable part protruding from the V-shaped sharp portion, and the backing layer and the drug layer may be formed sequentially on the removable part at both ends of the V-shaped portion.

The single-sided type and/or double-sided type patch attachable to the occlusal plane of posterior teeth according to another exemplary embodiment of the present disclosure may further include a wax layer in contact with the backing layer. The wax layer may prevent leakage of an active ingredient from the drug layer into the mouth. The wax layer may be formed on the drug layer or on the backing layer. The wax layer may allow easier attachment to the occlusal plane of the highly curved posterior teeth by increasing the flexibility of the patch. A patch further including the wax layer may have an increased thickness. It is difficult to prepare a patch with a thickness of 2 mm or larger due to the characteristics of a preparation process (solvent casting). A thickness of about 2 mm is necessary to improve attachability to molars and deliver the active ingredient to the every corner of the molars. However, it is difficult to manufacture a patch having a thickness of 2 mm or more by solvent casting. Therefore the wax layer can be added to provide a thickness favorable to the manufacturing process.

The wax layer may include one or more wax selected from a group consisting of beeswax, carnauba wax and paraffin wax. Specifically, it can improve the attachability to the occlusal plane of posterior teeth, which may be decreased due to the unevenness of the surface.

The patch attachable to the occlusal plane of posterior teeth of the present disclosure may be prepared by varying the type, content and tackiness of a polymer used in the backing layer of the patch, so that the patch can be attached well to the uneven occlusal plane and a drug (particularly, a fluorine-containing ingredient for preventing tooth decay, a peroxide-containing containing ingredient for whitening teeth, ingredients for protecting sensitive teeth such as KNOB, monopotassium phosphate, dipotassium phosphate, etc., *magnolia* extract having antibacterial effect, sodium bicarbonate for treating bad breath, etc.) can be delivered effectively to the surface of the teeth.

Specifically, the drug layer may include a pressure-sensitive adhesive polymer. The pressure-sensitive adhesive polymer (PSA polymer) refers to a polymer that can be attached to the surface of an adherend at room temperature in short time and with light pressure such as pressing with fingers, without using light, heat, water, solvent, etc. A variety of pressure-sensitive adhesive polymers are available. When considering the compatibility with the drug used in the drug layer, one or more pressure-sensitive adhesive polymer selected from a group consisting of an acrylic acid ester, a carboxylic acid, a polysiloxane and a synthetic or natural rubber may be used. Specifically, when a fluorine-containing ingredient for preventing tooth decay is used in the drug layer, a calcium-containing polymer cannot be used due to the compatibility issue.

Specifically, the PSA polymer may be included at a content of 0.1-10 wt %, more specifically 0.5-5 wt %, based on the total dry weight of the drug layer. Superior attachability to the occlusal plane may be achieved within the content range. The addition of an adequate amount of the PSA polymer allows the remaining part to remain on teeth as the backing layer is smoothly removed from the removable part during chewing due to the balance between the tackiness of the backing layer to the removable part and the tackiness of the drug layer to the teeth.

Specifically, the drug layer may include a drug ingredient, a wetting agent, a film former, a thickener, a foaming agent, an abrasive, etc., and ingredients used in the industry for preparing a tooth-attachable patch may be used without limitation. Specifically, the drug ingredient may generally include various drug ingredients that can be delivered orally. More specifically, it may include a fluorine-containing ingredient for preventing tooth decay. The wetting agent may include one or more selected from a group consisting of polypropylene glycol, polyethylene glycol and glycerin. Specifically, it may be glycerin when considering the compatibility with the PSA polymer. When considering the purpose of the present disclosure, the content of the wetting agent may be 5-30 wt % based on the total dry weight of the drug layer. When considering the purpose of the present disclosure, the film former may be specifically povidone in consideration of the compatibility with the PSA polymer. When considering the purpose of the present disclosure, the content of the film former may be 5-30 wt % based on the total dry weight of the drug layer. The thickener may be specifically pullulan when considering the compatibility with the PSA polymer. When considering the purpose of the present disclosure, the content of the thickener may be 0.1-10 wt % based on the total dry weight of the drug layer. The abrasive may specifically include silica abrasive.

In an exemplary embodiment of the present disclosure, the backing layer includes a water-insoluble polymer. The water-insoluble polymer may be one or more selected from a group consisting of polyethylene, polyvinyl acetate, ethyl cellulose, poly(methyl methacrylate), methacryloyl ethyl betaine/methacrylate copolymers and mixtures thereof. Specifically, it may be ethyl cellulose when considering the purpose of the present disclosure. The content of the water-insoluble polymer may be 5-15 wt % based on the total dry weight of the backing layer. Superior shape retention and superior attachability to the drug layer may be expected when the content is within the above range. The water-insoluble polymer may not include polyurethane.

Specifically, the backing layer may include, in addition to the water-insoluble polymer, a surfactant, a plasticizer, a wetting agent, etc., and the ingredients used in the industry for preparing a backing layer of a tooth-attachable patch can be used without limitation. Specifically, the surfactant may be one or more selected from a group consisting of SPAN20, SPAN40, SPAN60 and SPAN80. Specifically, SPAN80 may be used when considering the purpose of the present disclosure. The content of the surfactant may be 5-20 wt % based on the total dry weight of the backing layer. The plasticizer may include castor oil when considering the purpose of the present disclosure. The content of the plasticizer may be 5-20 wt % based on the total dry weight of the backing layer.

In an exemplary embodiment, it is intended to provide a patch wherein the drug layer of the patch is attached well to the occlusal plane but, once attached to the upper teeth, is not attached to the occlusal plane of the lower teeth due to the difference in the tackiness of the backing layer and the drug layer. The inventors of the present disclosure have identified the desired tackiness of the backing layer and the drug layer included in the patch, and provide a patch suitable to be used on the occlusal plane of posterior teeth. When the backing layer and the drug layer of the patch are cut to 1.2 cm×5 cm and then tested with a Zwick DE/1494 universal testing machine at a speed of 5 mm/s after attaching 2.5 cm onto a slide glass, the drug layer may have a tackiness of at least 50 gf and the backing layer may have a tackiness of 10-20 gf. More specifically, the drug layer may have a tackiness of 50-100 gf. Specifically, in the patch of the present disclosure, the tackiness of the drug layer may be 2 times of the tackiness of the backing layer. When the tackiness are within the above-described ranges, the tackiness between the drug layer and the teeth becomes stronger than the tackiness between the backing layer and the removable part and, therefore, the drug layer is attached well to the occlusal plane of posterior teeth and the backing layer is detached well from the occlusal plane of posterior teeth. Therefore the patch may be used conveniently.

The present disclosure provides a patch attached to the occlusal plane of posterior teeth, wherein a backing layer is formed on a drug layer and a removable part is formed thereon. The removable part may be a PET film. The drug layer of the patch of the present disclosure may further have a protective film.

The removable part may have a foldable structure so that the portion not in contact with the remaining part can be folded. The foldable structure is a structure that can be folded or unfolded, and the removable part may be folded, for example, as broken lines or wrinkles are formed. For example, FIG. 12 shows a linear-type patch with the removable part folded, and FIG. 13 shows a symmetric-type patch with the removable part folded. When the removable part is folded, consumers' usability may be improved through simplified packaging. In addition, the length of the handle part of the patch may be extended without increasing the size of the package. FIG. 14 shows a patch attachable to the occlusal plane of posterior teeth accommodated in a package. In an exemplary embodiment of the present disclosure, when the patch is packaged, it may be accommodated in the package up to the removable part which has also been mentioned as the handle and, when the removable part is accommodated in the package, the removable part may have the foldable structure mentioned above. In an exemplary embodiment of the present disclosure, when the patch is packaged, the removable part may not be accommodated in the package and only the part inserted into the mouth may be accommodated in the package. If the removable part is not accommodated in the package, cost saving may be expected because the packaging for product protection can be minimized. In addition, consumers can intuitively recognize the using parts and the handle part can be changed variously for the same packaging. The package can be prepared with any packing material commonly used in the industry for packaging of patches.

In another exemplary embodiment, the present disclosure provides a method for delivering a fluorine-containing ingredient for preventing tooth decay to posterior teeth by attaching the patch attachable to the occlusal plane of posterior teeth to the occlusal plane of posterior teeth. The removable part of the patch attachable to the occlusal plane of posterior teeth may be removed after the patch is pressed between upper and lower teeth. Through this, the drug layer may be attached to both the left and right posterior teeth in the mouth or only to the posterior teeth of one side. The drug layer may be attached to both the upper and lower posterior teeth of left and right sides, only to the upper and lower posterior teeth of the left side, or only to the upper and lower posterior teeth of the right side.

In an exemplary embodiment of the present disclosure, the patch attachable to the occlusal plane of posterior teeth may be provided after the drug layer or the drug layer and the backing layer are cut to be split into a plurality of pieces. In another exemplary embodiment, when a wax layer is added, it may be provided such that the patch including the wax layer is cut to be split into a plurality of pieces. The shape and size of the patch may be adjusted by a consumer according to the shape and size of his/her teeth, and the remaining part may be rearranged by the customer immediately before use depending on the shape and size of teeth or purpose of use. Specifically, FIG. 15 shows an example of a patch with the remaining part cut. For example, the remaining part may cut to have a grid or hexagonal pattern.

In an exemplary embodiment of the present disclosure, the patch may be removed by tooth brushing. For example, both the backing layer and the drug layer may be removed by tooth brushing 1-10 minutes after the attachment.

The patch of the present disclosure may be provided with a consumer manual containing the following instructions for use. After locating the patch according to an exemplary embodiment of the present disclosure between upper and lower molars, the remaining part of the patch is attached to the occlusal plane of molars by biting (chewing or pressing). Then, the removable part (handle layer) may be removed from the remaining part. Due to the difference in tackiness, only the removable part may be removed by pulling the handle part. Several minutes after the attachment, the patch may be removed by brushing with a toothbrush.

In an exemplary embodiment, the present disclosure provides a multi-layered tooth-attachable patch that can be attached to teeth, specifically incisors, canines, molars, etc. The multi-layered tooth-attachable patch has a handle. The multi-layered tooth-attachable patch is a patch consisting of at least two layers, specifically three, four, five, six or more layers depending on purpose.

In an exemplary embodiment, the present disclosure provides a multi-layered tooth-attachable patch including: a first layer including an adhesive polymer and a drug ingredient and attached to the surface of teeth; a second layer formed on the first layer and maintaining the shape of the first layer; and a third layer formed on the second layer and separated from the second layer, wherein the third layer has a handle formed to protrude upward, forward or backward. Specifically, the handle may be gripped with fingers when the third layer is removed or may prevent a drug included in the first layer from adhering to the fingers during attachment to teeth.

The first layer, which includes an adhesive polymer and a drug ingredient, is attached to the surface of teeth and may also be referred to as a drug layer. The first layer is attached to the surface of teeth and the drug included in the first layer may be released with time. The tackiness refers to the sticky property allowing attachment to the surface of teeth. The first layer of the tooth-attachable patch of the present disclosure may be sticky from the first time, or may not be sticky at first but become sticky after attachment due to water absorption.

Specifically, the adhesive polymer of the first layer may include a pressure-sensitive adhesive polymer. The pressure-sensitive adhesive polymer (PSA polymer) refers to a polymer that can be attached to the surface of an adherend at room temperature in short time and with light pressure such as pressing with fingers, without using light, heat, water, solvent, etc. A variety of pressure-sensitive adhesive polymers are available. When considering the compatibility with the drug used in the drug layer, one or more pressure-sensitive adhesive polymer selected from a group consisting of an acrylic acid ester, a carboxylic acid, a polysiloxane and a synthetic or natural rubber may be used. In addition, the first layer of the tooth-attachable patch of the present disclosure may further include a water-soluble or water-dispersible polymer. The term "water-soluble or water-dispersible polymer" used in the present specification refers to a polymer which is miscible or dispersible in an aqueous such as water either substantially or totally. For example, polyalkyl vinyl ether-maleic acid copolymer (PVM/MA copolymer; Gantrez AN 119, AN 139, S-97), polyvinyl alcohol, polyacrylic acid, poloxamer 407 (Pluronic, poly(ethylene oxide)-poly(propylene oxide)-poly(ethylene oxide) triblock copolymer), polyethylene oxide (Polyox), polyvinylpyrrolidone-vinyl acetate copolymer (PVP/VA copolymer; Luviskol VA, plasdone S, polyvinylpyrrolidone (PVP; K-15 to K-120), polyquaternium-11 (Gafquat 755N), polyquaternium-39 (Merquat plus 3330), carboxypolymethylene (Carbomer, Carbopol), hydroxypropyl methylcellulose, hydroxyethyl cellulose, hydroxypropyl cellulose, gelatin, sodium alginate, etc. may be used, although not being specially limited thereto. The adhesive polymer may be included at a content of specifically 0.1-10 wt %, more specifically 0.5-5 wt %, based on the total dry weight of the first layer. When the content is within the above range, superior attachability to teeth may be achieved. When the adhesive polymer is included in an adequate amount, the first layer and the second layer may remain on teeth after the third layer is removed due to the balance of the tackiness between the second layer and the third layer and the tackiness between the first layer and the teeth.

Specifically, the first layer my include a drug ingredient, a wetting agent, a film former, a thickener, a foaming agent, an abrasive, etc., and any ingredient used in the industry for preparing a tooth-attachable patch may be used without limitation. Specifically, the drug ingredient may include various drug ingredients that can be delivered through the mouth. Specifically, an ingredient for preventing tooth decay containing fluorine, etc. and an ingredient for whitening teeth containing hydrogen peroxide, etc. may be included. The wetting agent may include one or more selected from a group consisting of polypropylene glycol, polyethylene glycol and glycerin. Specifically, glycerin may be used when considering the compatibility with the adhesive polymer. When considering the purpose of the present disclosure, the content of the wetting agent may be 5-30 wt % based on the total dry weight of the first layer. Specifically, the film former may be povidone when considering the compatibility with the adhesive polymer. When considering the purpose of the present disclosure, the content of the film former may be 5-30 wt % based on the total dry weight of the first layer. Specifically, the thickener may be pullulan when considering the compatibility with the adhesive polymer. When considering the purpose of the present disclosure, the content of the thickener may be 0.1-10 wt % based on the total dry weight of the first layer. Specifically, the abrasive may be a silica abrasive.

The second layer, which is formed on the first layer, is used to maintain the shape of the first layer and may also be referred to as a backing layer. In an exemplary embodiment of the present disclosure, the second layer may include a water-insoluble polymer. The water-insoluble polymer may be one or more selected from a group consisting of polyethylene, polyvinyl acetate, ethyl cellulose, poly(methyl methacrylate), methacryloyl ethyl betaine/methacrylate copolymer and mixtures thereof. Specifically, ethyl cellulose may be used when considering the purpose of the present disclosure. The content of the water-insoluble polymer may be 5-15 wt % based on the total dry weight of the second layer. When the content is within the above range, superior maintenance of shape and superior attachability to the first layer may be expected. In an exemplary embodiment, the water-insoluble polymer may not include polyurethane.

Specifically, the second layer may include, in addition to the water-insoluble polymer, a surfactant, a plasticizer, a wetting agent, etc. and any ingredient used in the industry of preparing a tooth-attachable patch for preparing the second layer for backing the drug ingredient-including first layer may be used without limitation. Specifically, the surfactant may be one or more selected from a group consisting of SPAN20, SPAN40, SPAN60 and SPAN80. Specifically, SPAN80 may be used when considering the purpose of the present disclosure. The content of the surfactant may be 5-20 wt % based on the total dry weight of the second layer. The plasticizer may include castor oil when considering the purpose of the present disclosure. The content of the plasticizer may be 5-20 wt % based on the total dry weight of the second layer.

The size or area of the first layer and the second layer may be adjusted adequately according to the size and area of the teeth to which the patch is attached.

The third layer is formed on the second layer and is separated from the second layer. The third layer has a handle which is formed to protrude upward, forward or backward from the third layer. The handle is gripped with fingers when the third layer is removed. The 'handle' refers to a portion which can be gripped with fingers to remove the patch from the surface of teeth. The shape or size of the handle is not specially limited. The handle may be integrated with the third layer or may be prepared separately and then attached to the third layer. The handle and the third layer may be prepared from the same or different materials. In order to stably separate the third layer from the second layer by gripping the handle with fingers, the handle may be integrated with the third layer and may be prepared with the same material as the third layer, although the scope of the present disclosure is not specially limited thereto. Specifically, one or more selected from a group consisting of polyethylene terephthalate (PET), polyethylene (PE), nonwoven, paper, synthetic or natural rubber, nylon and thermoplastic polyurethane may be used. The 'upward' from the third layer refers to a direction perpendicular to a plane at which the third layer is not in contact with the second layer. FIG. 16 shows an example of a multi-layered patch wherein a handle is formed 'upward' from the third layer. The upward direction may refer to the direction indicated by (a) in FIG. 16. The position of the handle may be changed leftward or rightward depending on the site where the patch is attached. In another exemplary embodiment, the number of the handle 301 formed 'upward' from the third layer may be two or larger. The 'forward' or 'backward' from the third layer refers to a direction protruding horizontally from the edge of the third layer. In FIG. 16, (b) may be understood as 'forward', and (c) may be understood as 'backward'. FIG.

17 shows an example of a multi-layered patch wherein a handle 311 is formed 'forward' or 'backward' from the third layer. Referring to FIG. 17, a tooth-attachable patch is provided wherein a second layer 200 is formed on a first layer 100 and a handle 311 extends from a part of a third layer 310 formed thereon. The surface of the first layer 100 is protected by a protective layer 400. FIG. 18 shows an exemplary embodiment wherein the handle 311 extending from a part of the third layer 310 has a round shape.

In the tooth-attachable patch, the protective layer 400 protecting the first layer 100 wherein the drug is stored may be formed on one side of the first layer to have an area which is the same as or larger than that of the first layer. FIG. 20 shows an exemplary embodiment wherein a protective layer 410 is formed on a drug layer 100 to have a larger area. The protective layer 400 or 410 may be removed when the first layer 100 is attached to the surface of teeth. The material constituting the protective layer 400 or 410 is not specially limited and the same material as that of a third layer 300 may be used. For example, aluminum, polyethylene terephthalate (PET), polyethylene (PE), nonwoven, paper, etc. may be used. FIG. 19 shows a state wherein the protective layer 400 is removed before attaching the multi-layered patch according to an exemplary embodiment of the present disclosure to the surface of teeth. The protective layer may have a larger area than the drug layer for convenient removal before the use of the patch. FIG. 20 shows such an exemplary embodiment.

In an exemplary embodiment, if the third layer is extended to have a larger area than the second layer and the extended portion can be gripped with fingers, the extended portion may become a handle 321. FIG. 21 shows such an exemplary embodiment. FIG. 21 shows an exemplary embodiment of a patch wherein a protective layer 400 protecting a first layer and a third layer 320 and an extended portion 321 of the third layer functions as a handle. Such a structure allows easy removal of the protective layer 410 from the first layer 100 before use and also allows easy removal of the third layer 320 from the second layer 200 after predetermined time has passed after attachment of the patch.

In an exemplary embodiment of the present disclosure, the handle formed upward from the third layer 300 may be formed as the third layer extends upward or a handle structure is attached upward from the third layer. The extension upward from the third layer means that the handle is formed of the same material as the third layer and the third layer has a protruding structure at the side opposite to the side in contact with the second layer. FIG. 22 shows an exemplary embodiment wherein a patch with a handle formed upward from the third layer is attached. Referring to FIG. 22, a protruding handle 301 is at the center portion of the patch. After the drug layer 100 is attached to the surface of teeth and predetermined time has passed, the third layer 300 may be separated from the second layer 200 by pulling the protruding handle 301 at the center portion.

The handle 311 formed forward or backward from the third layer may be formed as the third layer extends forward or backward or a handle structure is attached forward or backward from the third layer. Specifically, the handle of the third layer may be formed forward or backward from the third layer at one or both sides with an area that can be gripped with fingers. FIG. 23 shows an exemplary embodiment wherein a patch with a handle 311 formed forward or backward from the third layer is attached. Referring to FIG. 23, the handle 311 extends horizontally from the third layer 310 of the patch. After the patch has been attached to teeth, the third layer 310 may be separated from the second layer 200 by gripping the handle.

The tackiness of the patch may be measured with a Zwick DE/1494 universal testing machine at a speed of 5 mm/s after cutting the patch to 1.2 cm×5 cm and attaching 2.5 cm onto a slide glass by pressing with a 1 kg weight for 10 seconds.

The tackiness between teeth and the first layer is approximately 200 gf or higher, and the tackiness between the second layer and the third layer is lower than the tackiness between the teeth and the first layer to separate the third layer. Specifically, the tackiness between the second layer and the third layer may be 90% or lower, 80% or lower, 70% or lower, 60% or lower, 50% or lower, 40% or lower, 30% or lower, 20% or lower or 10% or lower as compared to the tackiness between the first layer and the teeth. Specifically, easy removal may be possible when the tackiness is 60% or lower. For example, if the tackiness between the first layer and the teeth is 400 gf or 200 gf, the tackiness between the second layer and the third layer may be 360 gf or lower or 180 gf or lower, respectively, and preferably it may be manufactured to have the difference in tackiness of 2 times or more. Specifically, the tackiness between the second layer and the third layer may be half the tackiness between the first layer and the teeth. For example, if the tackiness between the first layer and the teeth is 400 gf, the tackiness between the second layer and the third layer may be 200 gf. For example, the tackiness between the second layer and the third layer measured by the above method may be about 100 gf. Here, 'about' means a range of ±10, ±9, ±8, ±7, ±6, ±5, ±4, ±3, ±2, ±1, ±0.5 or ±0.1. If the tackiness between the first layer and the surface of teeth is stronger than the tackiness between the second layer and the third layer, only the third layer may be separated with the patch remaining attached when the third layer is separated from the second layer. Therefore, it may be desired that the tackiness are within the above-described ranges. Also, when the tackiness are within the above-described ranges, the patch may be used conveniently without unwanted detachment when distributed in the market.

FIG. 24 shows an exemplary embodiment of the present disclosure. A handle 331 may be formed forward or backward from the third layer at one side with an area that can be gripped with fingers, or two handles may be formed at both sides. As shown in FIG. 24, the handle 331 formed at the end portion of the edge of the third layer may be removed easily even with weak force.

The patches having handles 301, 311, 321, 331 according to various exemplary embodiments of the present disclosure can be attached to the surface of teeth without the drug adhering to fingers and can be removed sanitarily without touching the gum or teeth with fingers.

In an exemplary embodiment of the present disclosure, the patch may be removed by tooth brushing. Specifically, the patch may be removed by tooth brushing 1-60 minutes after attachment depending on the attached site. For example, both the second layer and the first layer may be removed by tooth brushing 1-10 minutes after the attachment. As another example, both the second layer and the first layer may be removed by tooth brushing 30-60 minutes after the attachment. Specifically, for the patch attached to molars, both the second layer and the first layer may be removed by tooth brushing 1-10 minutes after the attachment. And, for the patch attached to incisors and/or canines, both the second layer and the first layer may be removed by tooth brushing 30-60 minutes after the attachment.

The patch of the present disclosure may be provided with a consumer manual containing the following instructions for use. The protective layer is removed before attaching the patch according to an exemplary embodiment of the present disclosure to the surface of teeth. Then, the handle is gripped and the first layer of the patch is attached to the surface of teeth. Then, the third layer may be removed from the second layer by gripping the handle of the patch. The second layer may be removed at any time between immediately after the attachment of the patch and after the drug of the first layer has been completely released, according to user convenience. Due to the difference in the tackiness between the teeth and the first layer and the tackiness between the second layer and the third layer, the third layer may be removed from the second layer by gripping and pulling the handle. Several minutes after the attachment, the patch may be removed by brushing with a toothbrush.

Advantageous Effects

The present disclosure provides a patch which is attached to the occlusal plane of teeth by chewing and effectively delivers an active ingredient with improved user convenience.

The present disclosure provides a patch that can be easily attached to the occlusal plane of teeth simply by chewing.

The present disclosure provides a patch equipped with a handle, which can be easily attached to the occlusal plane of posterior teeth.

The patch of the present disclosure can be easily attached to the occlusal plane of posterior teeth simply by chewing. Although the patch adheres well to the occlusal plane and is not easily detached, it can be easily removed by applying force sideways.

The patch of the present disclosure can have a thickness which is difficult to achieve with the existing solvent casting by using a wax layer, and can be easily attached to the uneven occlusal plane of posterior teeth.

The patch of the cut structure may maintain the shape of the patch due to the handle structure of the removable part even if the remaining part exists in a split (or fragmented) state, and it is independent of the size and shape of the teeth since the remaining part may be attached to the teeth in a split (or fragmented) state.

The patch of the present disclosure can be attached and removed easily due to a handle structure. It prevents the drug from adhering to fingers and allows sanitary removal of the patch without touching the gum or teeth.

DESCRIPTION OF DRAWINGS

The present disclosure should not be construed as being limited to the following drawings.

In FIG. 16, (a) indicates an upward direction, (b) indicates a forward direction and (c) indicates a backward direction.

BEST MODE

Figure 1:
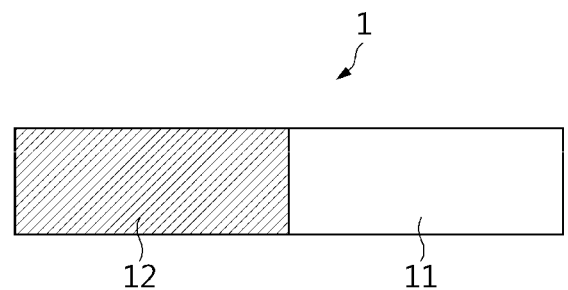
FIG. 1 shows a linear-type patch 1 consisting of a remaining part 12 and a removable part 11.
Figure 2:
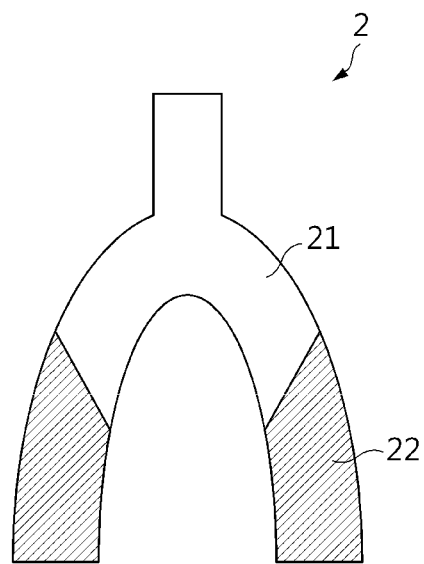
FIG. 2 shows a symmetric-type U-shaped patch as an example of a symmetric-type patch 2.
Figure 3:
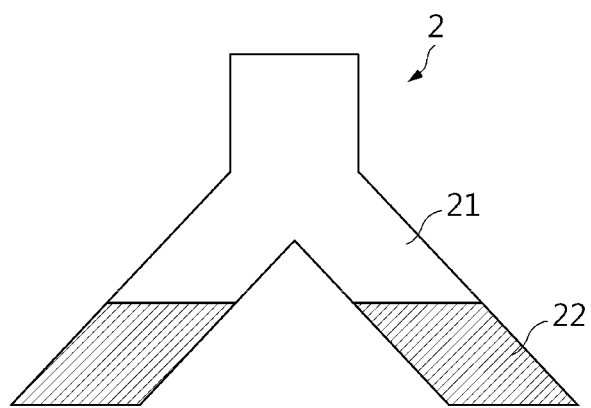
FIG. 3 shows a symmetric-type V-shaped patch as an example of a symmetric-type patch 2.
Figure 4:
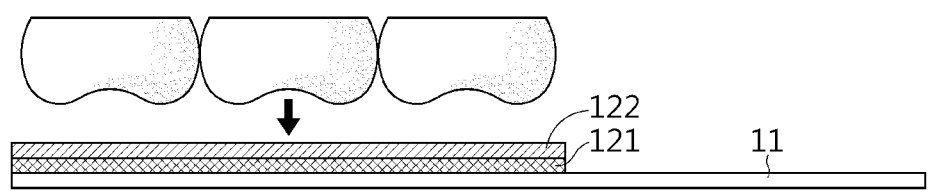
FIG. 4 schematically shows the attachment of a single-sided type patch to the occlusal plane of posterior teeth. A removable part 11 is removed after a drug layer 122 is attached to the occlusal plane of posterior teeth.
Figure 5:
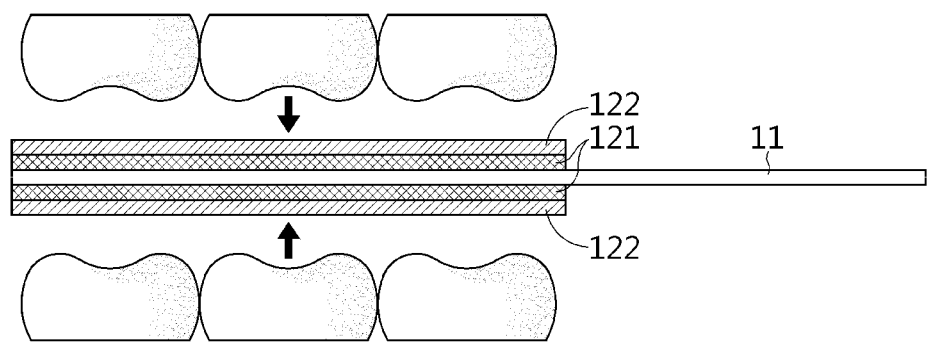
FIG. 5 schematically shows the attachment of a double-sided type patch to the occlusal plane of posterior teeth. A backing layer 121 and a drug layer 122 are formed sequentially on both sides of a removable part 11. After the drug layer 122 comes in contact with upper and lower posterior teeth, the removable part 11 is detached and removed from the each backing layer 121.
Figure 6:
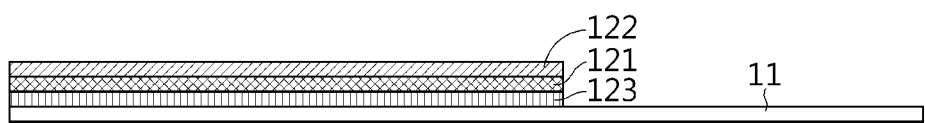
FIG. 6 shows a wax layer 123 disposed between a backing layer and a removable part.
Figure 7:
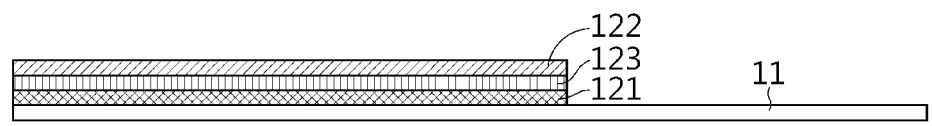
FIG. 7 shows a wax layer 123 disposed between a backing layer 121 and a drug layer 122 of a remaining part.
Figure 8:
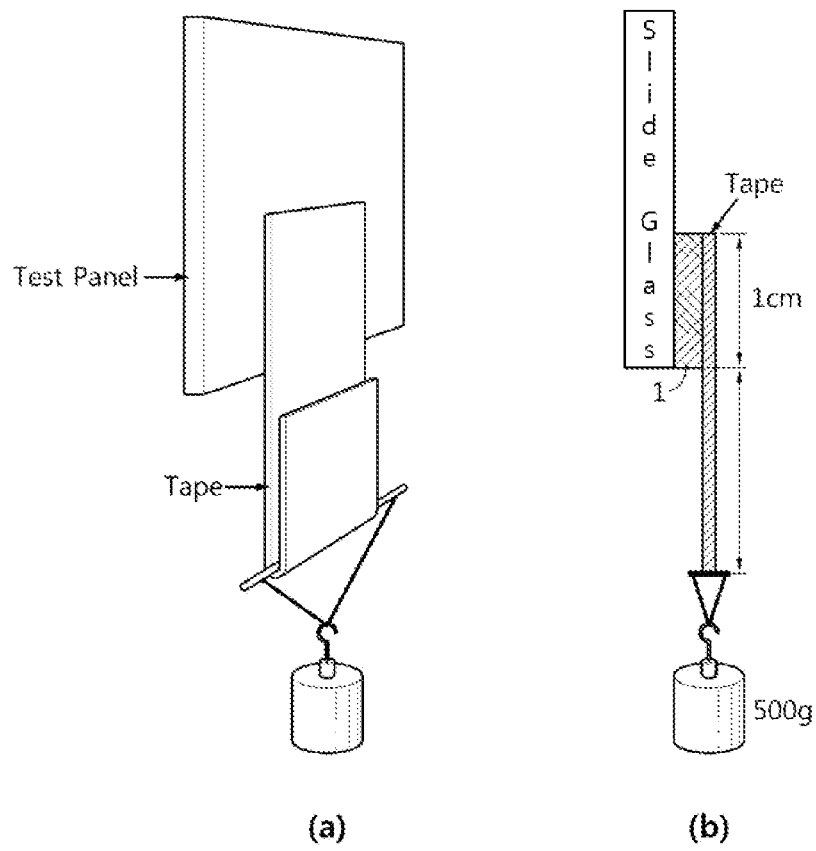
FIG. 8 schematically shows shear testing. (a) and (b) schematically show the testing of the tackiness of a patch.
Figure 9:
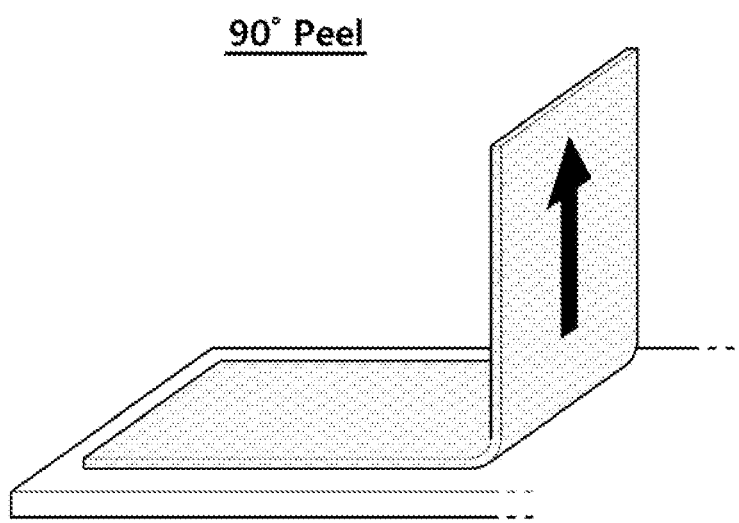
FIG. 9 schematically shows 90° peel-off testing.
Figure 10:
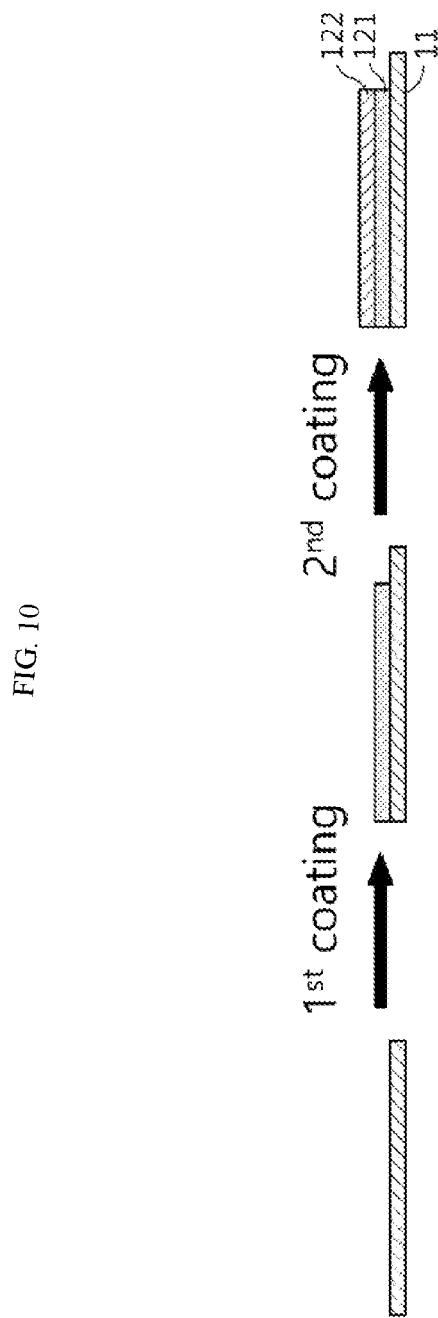
FIG. 10 shows a process of preparing a patch consisting of a remaining part and a removable part according to an exemplary embodiment of the present disclosure.
Figure 11:
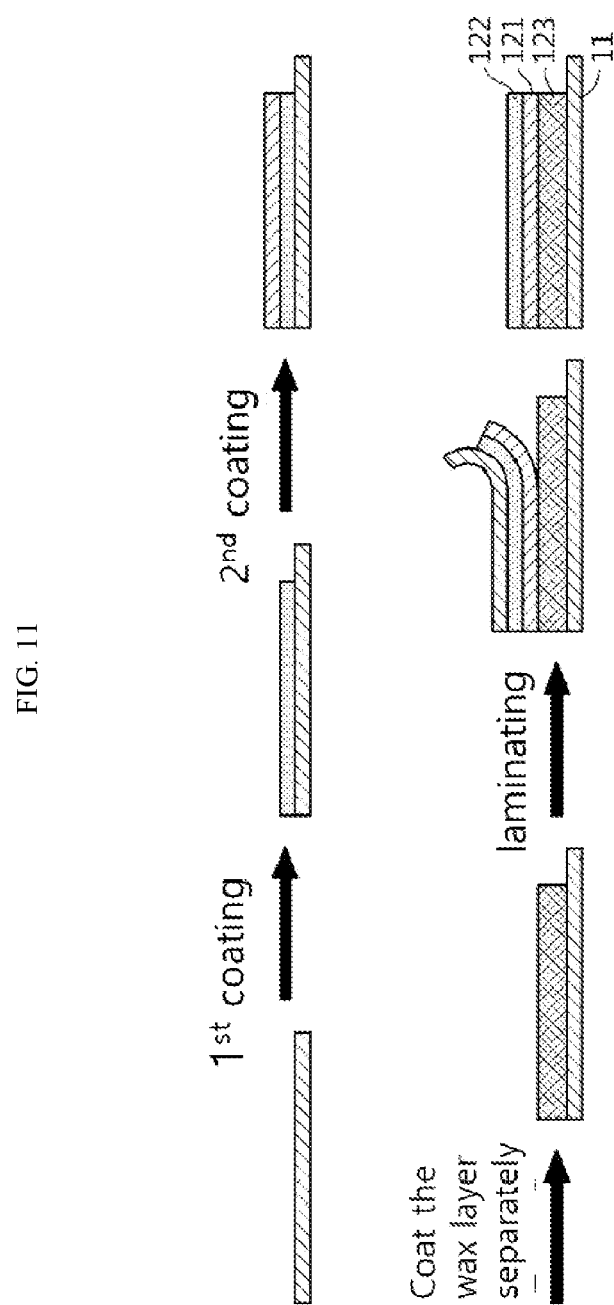
FIG. 11 shows a process of preparing a patch further including a wax layer according to an exemplary embodiment of the present disclosure. A drug layer is first coated on a substrate (PET), and a backing layer is coated thereon. Separately, a wax layer is coated on the removal part (PET). After that, the backing layer and the wax layer may be laminated and then aged at high temperature.
Figure 12:
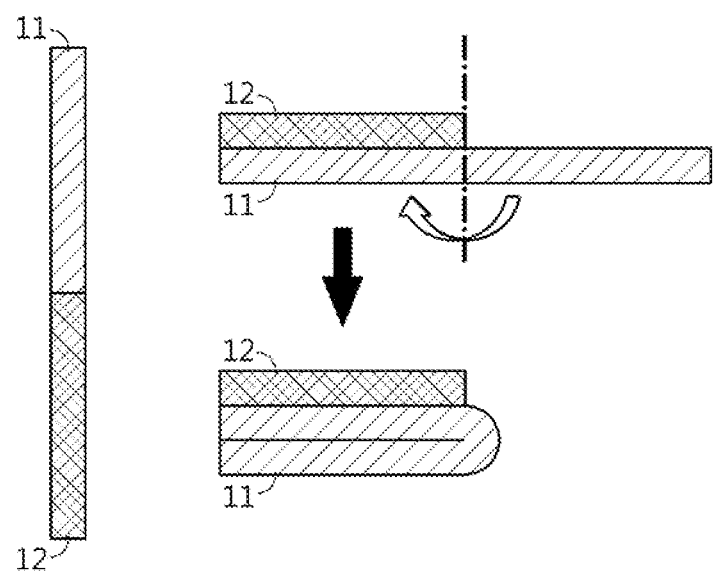
FIG. 12 shows a state where a removable part of a linear-type patch is folded.
Figure 13:
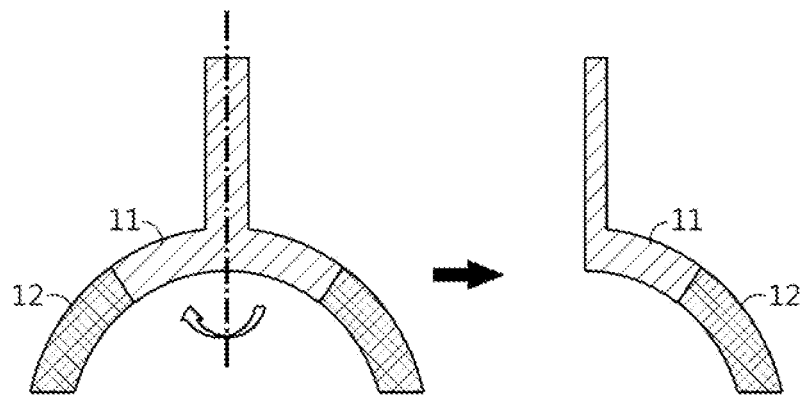
FIG. 13 shows states where a removable part of a symmetric-type patch is folded. A shows a state where a removable part is folded symmetrically, and B shows a state where a handle of the removable part is folded along the direction of a remaining part.
Figure 13:
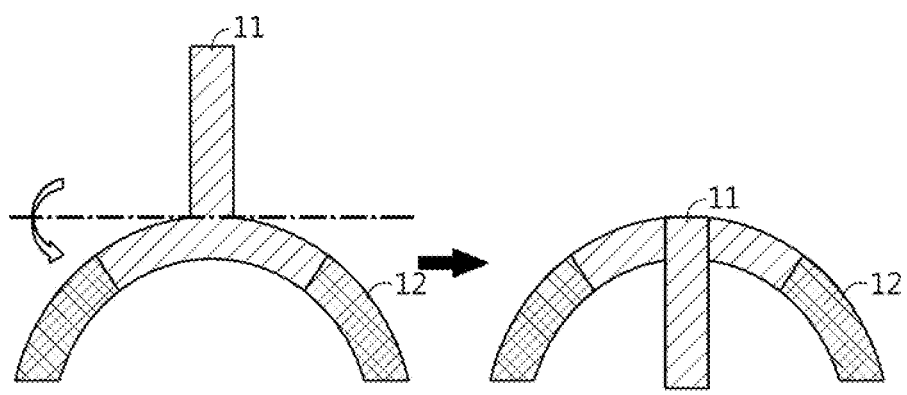
Figure 14:
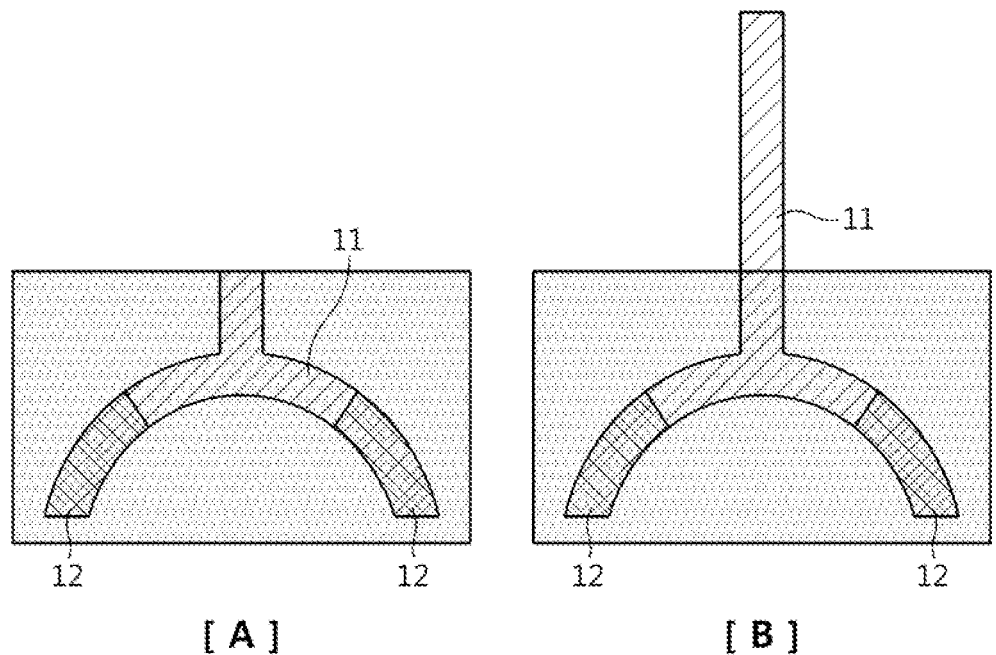
FIG. 14 shows a state where patches attachable to the occlusal plane of posterior teeth are accommodated in a package. A shows that up to a removable part can be accommodated in the package, and B shows that only the portion inserted in the mouth may be accommodated in the package. The package is indicated as a shaded rectangle.
Figure 15:
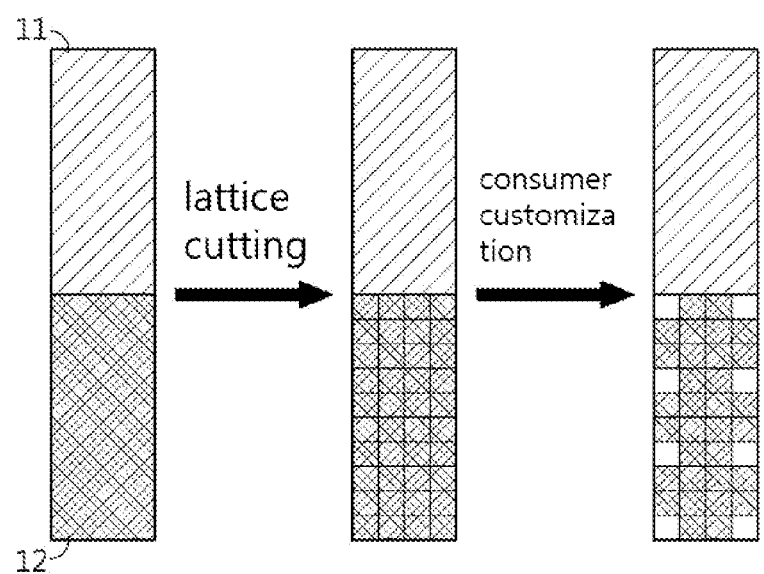
FIG. 15 shows a patch according to an exemplary embodiment of the present disclosure wherein a remaining part is cut. The remaining part may be cut with grid patterns to have a desired shape for use on teeth.
Figure 16:
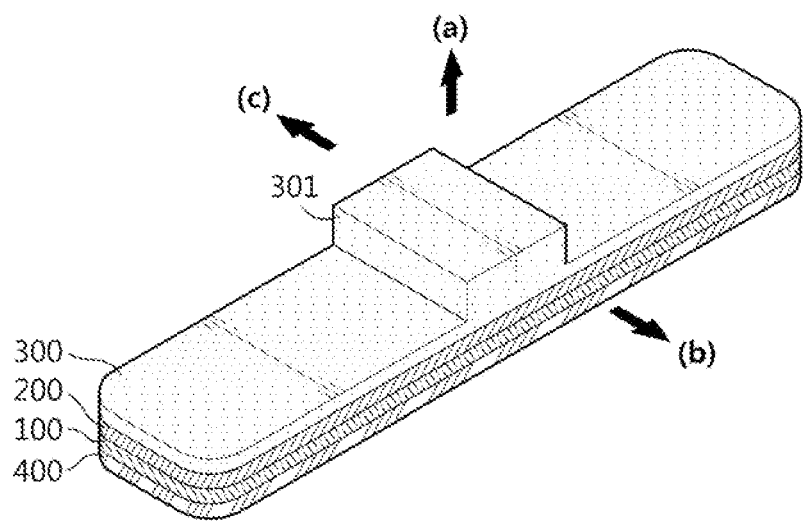
FIG. 16 shows a multi-layered patch according to an exemplary embodiment of the present disclosure wherein a handle is formed 'upward' from a third layer.

The present disclosure is described in more detail referring to the following examples. However, they are not intended to limit the scope of the present disclosure. Those having ordinary knowledge in the art will be able make various changes and modifications to the present disclosure within the scope of the present disclosure.

1. Preparation of Patch Attachable to Occlusal Plane of Posterior Teeth, Consisting of Remaining Part Consisting of Drug Layer and Backing Layer and Removable Part A. Composition and Preparation A solution for preparing a drug layer and a solution for preparing a backing layer were prepared according to the compositions described in Table 1. After pouring the backing layer solution on a removable part formed from a PET film, the drug layer solution was poured thereon and then laminated by drying. A hydrophobic plasticizer (castor oil, SPAN80) of the backing layer may be joined on the PET. Subsequently, the PET was cut into a shape of a handle and the unnecessary part was removed. In Table 1, the contents are in wt % units, and the values within parentheses indicate the contents of the ingredients based on total weight of each layer after drying.

TABLE 1

| Drug layer | Content (content after drying) | Function | Backing layer | Content (content after drying) | Function |
|---|---|---|---|---|---|
| Sodium fluoride | 0.18% (0.22%) | Drug ingredient | Ethyl cellulose | 10% (15%) | Film former |
| Glycerin | 3.0% (10%) | Wetting agent | SPAN80 | 5% (10%) | Surfactant |
| Povidone | 15.0% (30%) | Film former | Castor oil | 5% (10%) | Plasticizer |
| Pullulan | 1.0% (2%) | Thickener | Glycerin | 5% (10%) | Wetting agent |
| SLS | 2.0% (2%) | Foaming agent | Ethanol, etc. | To 100% | Solvent |
| Carbomer | 1.0% (1%) | PSA | HPMC | 10% (15%) | Film former |
| Silica abrasive | 3.0% (10%) | Abrasive | Povidone | 10% (15%) | Film former |
| Water, etc. | To 100% | Solvent | | | |

PSA: acrylic acid ester, carboxylic acid, polysiloxane, rubber (natural, synthetic, etc.)

A linear-type patch and a U-shaped patch were prepared according to the above-described method.

B. Evaluation of Tackiness (1) Shear Test (PSTC 107 Standard)

(a) Test Method

The patch was cut to a size of 1.0 cm×1.0 cm and attached at the end of a slide glass by pressing for 10 seconds using a 1 kg weight. After cutting a Scotch tape to a size of 1.0 cm×4.0 cm and attaching onto the patch, the portion extending out of the patch (1.0 cm×3 cm) was folded in half and a 500 g weight was hung. Then, the time (seconds) taken until the patch was detached was measured.

A longer time can be interpreted as higher tackiness of the patch.

(For reference, the maximum biting force of molars is 122 kg/cm$^2$ on average for male adults (V Jain et al. (2014), A preliminary study to find out maximum occlusal bite force in Indian individuals, *Indian Journal of Dental Research*, 25(3), 325-330).

(b) Test Result

The shear test result is shown in Table 2. As can be seen from Table 2, the patch showed tackiness of 20 seconds or longer on average.

TABLE 2

| No. | 1 | 2 | 3 | 4 | 5 | 6 | 7 | Mean |
|---|---|---|---|---|---|---|---|---|
| Time (sec) | 25 | 26 | 31 | 23 | 15 | 17 | 18 | 22 |

(2) 90° Peel-Off Test (a) Test Method

The patch was cut to a size of 1.2 cm×5 cm and 2.5 cm of the side of the drug layer was attached onto a slide glass. Then, after pressing with a 1 kg weight for 10 seconds, the force required to remove the drug layer by pulling the portion of the patch not attached to the slide glass at a speed of 5 mm/s was measured using a Zwick DE/1494 universal testing machine.

(b) Test Result

The peel-off test result is shown in Table 3. As can be seen from Table 3, the drug layer of the patch had a tackiness of 50 gf or higher and 100 gf or lower on average.

TABLE 3

| No. | 1 | 2 | 3 | 4 | 5 | 6 | Mean |
|---|---|---|---|---|---|---|---|
| Force (gf) | 53.24 | 52.9 | 46.55 | 68.2 | 47.33 | 42.6 | 51.80 |

2. Preparation of Patch Attachable to Occlusal Plane of Posterior Teeth, Consisting of Remaining Part Consisting of Drug Layer, Backing Layer and Wax Layer and Removable Part A wax layer may be formed between a drug layer and a backing layer or between the backing layer and a removable part. In this example, a patch having a wax layer formed between a backing layer and a removable part was prepared.

The tackiness of the patch further including the wax layer was evaluated.

Test method: After sufficiently applying a dye on model molars, the drug layer of the patch was placed thereon and then pressed with a force of 5 kg/cm$^2$ for 5 seconds. Then, after removing the molars from the patch, the area of the dye remaining on the patch was measured.

A patch prepared by the existing solvent casting method has the problem that, if the thickness is 2 mm or larger, there is a risk of skinning phenomenon and it is difficult to maintain the shape. When a wax layer is included in the patch, the thickness may be increased and superior attachability may be achieved due to the flexibility of the wax material.

The depth on the uneven surface of the molars was set to 2.05±0.3 mm (A Arruda et al. (2007), Occlusal Fossae Depth of Permanent First Molars Assessed by Visual Examination: An In Vitro Approach, *Pediatric Dentistry*, 30(1), 19-24).

The result of evaluating the attachability of the uneven surface is shown in Table 4. As can be seen from Table 4, the patch having the drug layer had a tackiness of 50 gf or higher and 100 gf or lower. The attachability was improved as the thickness was larger.

TABLE 4

| Thickness of patch including wax layer | 300 μm | 2000 μm |
|---|---|---|
| Area of attachment (%) | 30.7 ± 7.3 | 74.8 ± 4.4 |

2. Preparation of Patch Attachable to Occlusal Plane of Posterior Teeth, Consisting of Remaining Part Consisting of Drug Layer, Backing Layer and Wax Layer and Removable Part A wax layer may be formed between a drug layer and a backing layer or between the backing layer and a removable part. In this example, a patch having a wax layer formed between a backing layer and a removable part was prepared.

3. Difference in Tackiness of Drug Layer and Backing Layer of Patch to Occlusal Plane A patch was prepared without a removable part such that the tackiness of a drug layer was 2 times or higher as compared to the tackiness of a backing layer. Then, 90° peel-off test was performed on the drug layer and the backing layer of the patch. The difference in tackiness is shown in Table 5.

TABLE 5

| Layer | Drug layer | Backing layer |
|---|---|---|
| Tackiness (gf) | 51.80 | 13.8 |

If the tackiness of the drug layer is not 2 times or higher as compared to the tackiness of the backing layer, the drug layer of the patch may remain on PET without being attached to the occlusal plane of posterior teeth when chewed. The patch of the present disclosure was detached well from the PET and attached well to the surface of teeth.

4. Preparation of Patch for Whitening Teeth Having Handle

A. Composition and Preparation (1) Preparation of Patch 1 (a Patch for Whitening Teeth Having Handle)

A solution for preparing a first layer (drug layer) and a solution for preparing a second layer (backing layer) were prepared according to the compositions described in Table 6. After pouring the second layer (backing layer) solution on a third layer formed from a PET film and drying the same, the first layer (drug layer) solution was poured thereon and then laminated by drying. A hydrophobic plasticizer (castor oil, SPAN80) of the second layer may be joined on the PET. Subsequently, the PET was cut into a shape of a handle and the unnecessary part was removed. In Table 6, the contents are in wt % units, and the values within parentheses indicate the contents of the ingredients based on total weight of each layer after drying. A patch for whitening teeth having a handle was prepared according to the above-described method.

TABLE 6

| First layer | Content (content after drying) | Function | Second layer | Content (content after drying) | Function |
|---|---|---|---|---|---|
| Hydrogen peroxide | 10.5% (3%) | Drug ingredient | Ethyl cellulose | 10% (15%) | Film former |
| Glycerin | 3.0% (10%) | Wetting agent | SPAN80 | 5% (10%) | Surfactant |
| Povidone | 15.0% (30%) | Film former | Castor oil | 5% (10%) | Plasticizer |
| Pullulan | 1.0% (2%) | Thickener | Glycerin | 5% (10%) | Wetting agent |
| SLS | 2.0% (2%) | Foaming agent | Ethanol, etc. | To 100% | Solvent |
| Carbomer | 1.0% (1%) | PSA polymer | HPMC | 10% (15%) | Film former |
| Silica abrasive | 3.0% (10%) | Abrasive | Povidone | 10% (15%) | Film former |
| Water, etc. | To 100% | Solvent | | | |

PSA: acrylic acid ester, carboxylic acid, polysiloxane, rubber (natural, synthetic, etc.)

(2) Preparation of Patch 2 (Patch for Whitening Teeth Having Handle)

Figure 17:
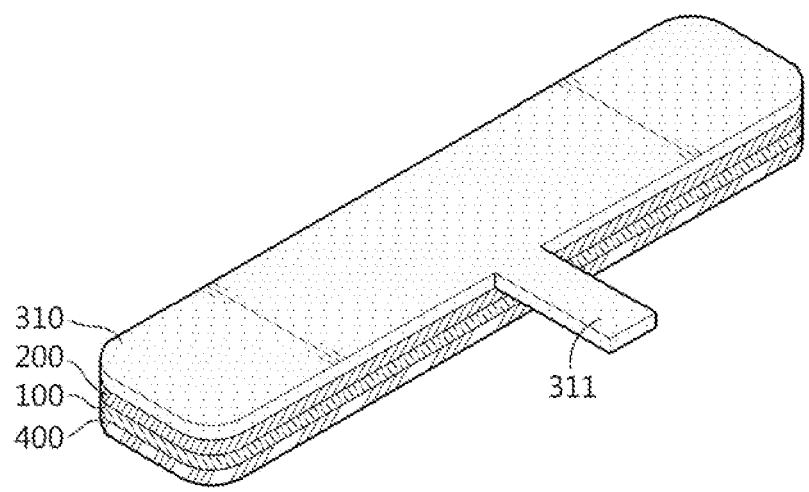
FIG. 17 shows a multi-layered patch according to an exemplary embodiment of the present disclosure wherein a handle is formed 'forward' or 'backward' from a third layer.
Figure 18:
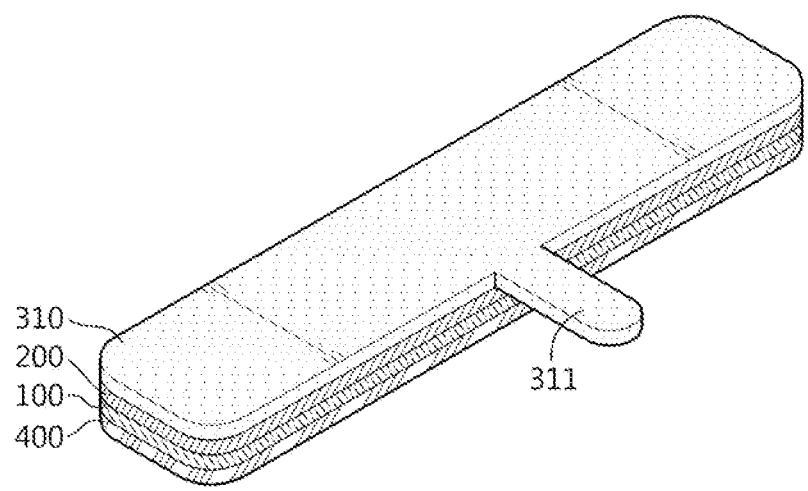
FIG. 18 shows a patch having handle modified to have a round shape
Figure 19:
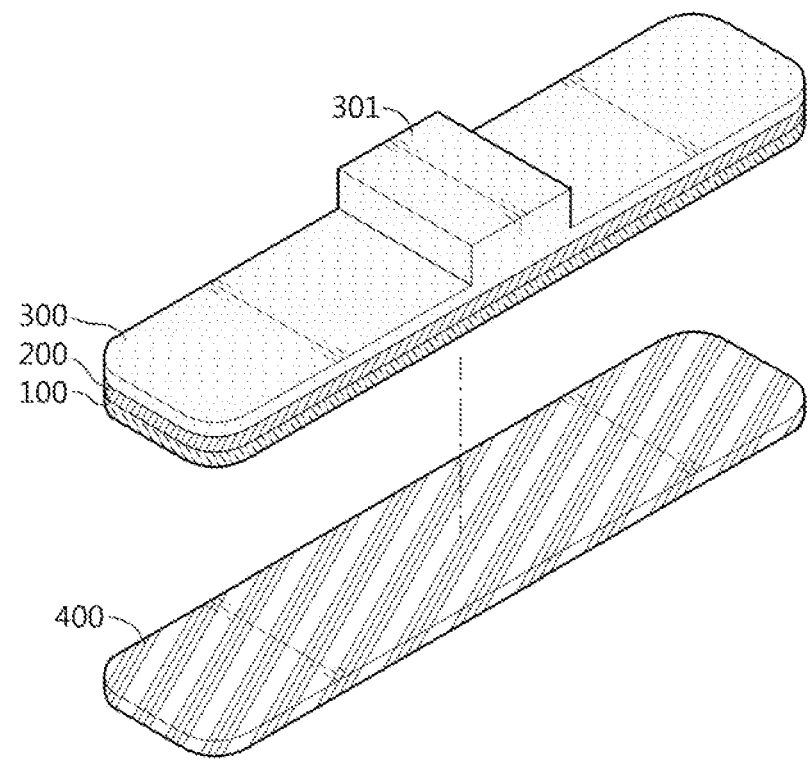
FIG. 19 shows a multi-layered patch according to an exemplary embodiment of the present disclosure in a state where a protective layer is separated before attachment to the surface of teeth.
Figure 20:
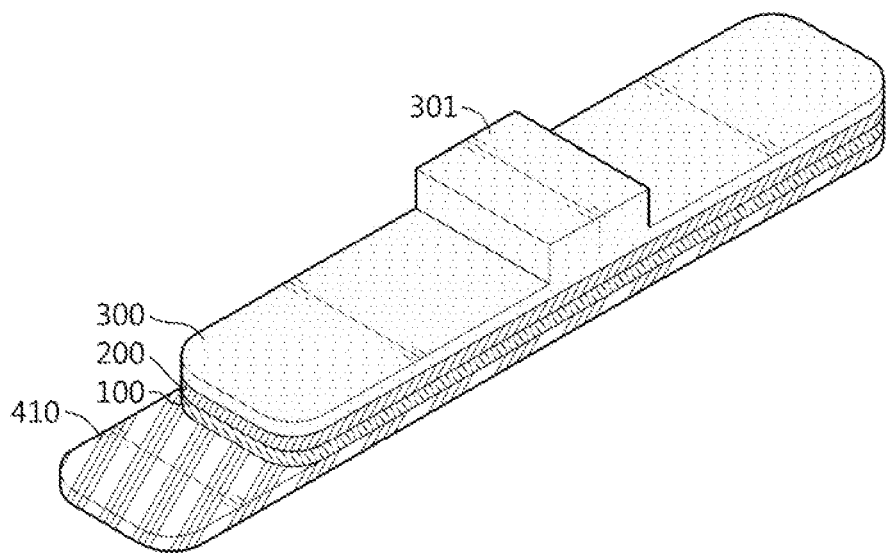
FIG. 20 shows a multi-layered patch having a protective layer according to an exemplary embodiment of the present disclosure, wherein the protective layer has a larger area than a first layer.
Figure 21:
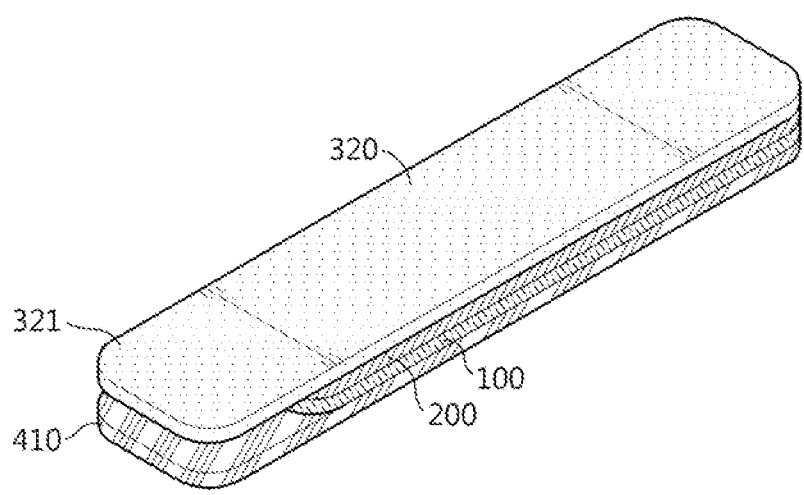
FIG. 21 shows a patch according to an exemplary embodiment of the present disclosure wherein a protective layer protecting a first layer and a third layer are extended so that the extended portion of the third layer can function as a handle.
Figure 22:
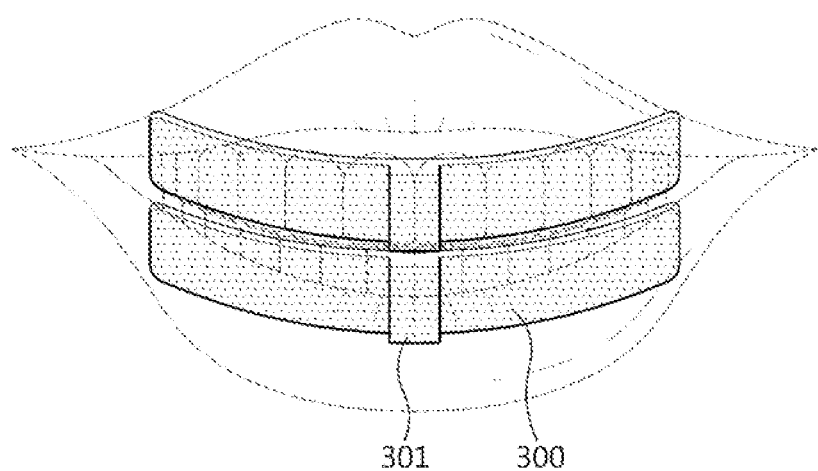
FIG. 22 shows a patch according to an exemplary embodiment of the present disclosure in a state where the patch having a handle formed upward from a third layer is attached to teeth.
Figure 23:
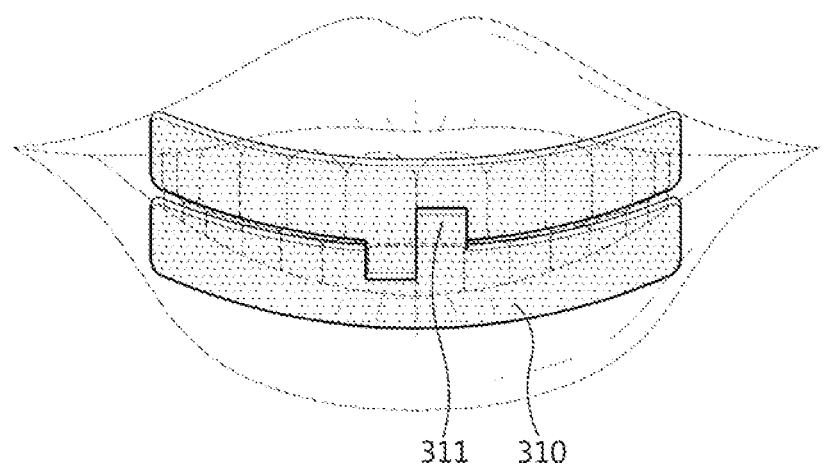
FIG. 23 shows a patch according to an exemplary embodiment of the present disclosure in a state where the patch having a handle formed forward or backward from a third layer is attached to teeth.
Figure 24:
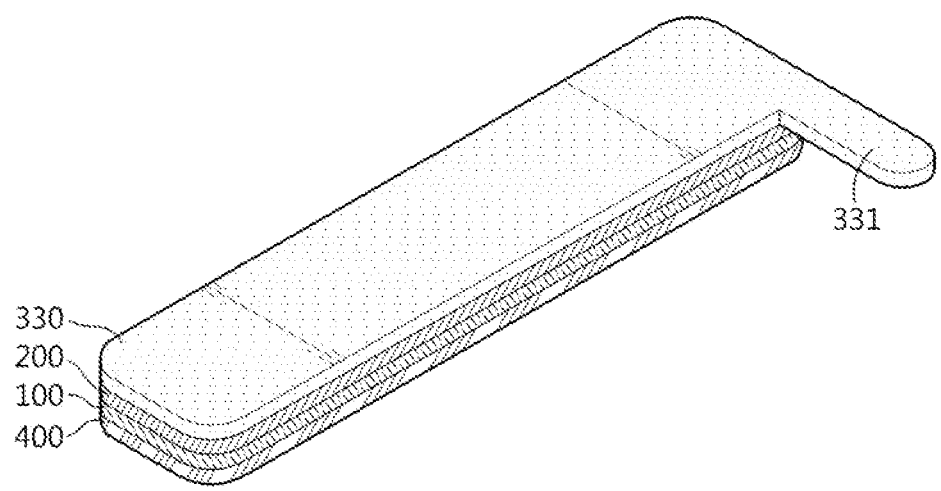
FIG. 24 shows a patch according to an exemplary embodiment of the present disclosure wherein a handle is formed at one side of a third layer.

A solution for preparing a first layer (drug layer) and a solution for preparing a second layer (backing layer) were prepared according to the compositions described in Table 6. After pouring the second layer (backing layer) solution on a PET film (third layer) with a handle disclosed in FIG. 17 and drying the same, the first layer (drug layer) solution was poured thereon and then laminated by drying to prepare a tooth-attachable patch for whitening teeth with a handle formed.

(3) Preparation of Patch for Whitening Teeth Having No Handle

A patch for whitening teeth with no handle was prepared according to the compositions described in Table 6.

The patches for whitening teeth 1 and 2 with handles prevented the drug from adhering to fingers when attached the surface of teeth and could be removed conveniently owing to the handles.

DETAILED DESCRIPTION OF MAIN ELEMENTS

1: Linear-type patch
2: Symmetric-type patch
11: Removable part of linear-type patch
12: Remaining part of linear-type patch
121: Backing layer of patch
122: Drug layer of patch
123: Wax layer of patch
21: Removable part of symmetric-type patch
22: Remaining part of symmetric-type patch
100: First layer 200: Second layer
300: Third layer
400: Protective layer
301: Handle formed upward from third layer of patch
311: Handle formed forward from third layer of patch
321: Handle formed as third layer extends to have larger area than second layer
331: Handle formed at one side forward from third layer of patch
410: Protective layer with increased area

INDUSTRIAL APPLICABILITY

The present disclosure provides a patch that can effectively deliver a drug ingredient to molars. The present disclosure provides a patch having a handle, which can be easily removed from teeth.

What is claimed is:

1. A patch attachable to the occlusal plane of posterior teeth, comprising:
   a drug layer;
   a backing layer in contact with the drug layer; and
   a removable part in contact with the backing layer, at least a portion of the removable part being separable from the backing layer,
   wherein the backing layer is located between the drug layer and the removable part such that the drug layer is not exposed to the removable part,
   wherein the backing layer includes a first backing layer on a first side of the removable part and a second backing layer on a second side of the removable part opposite the first side of the removable part, and wherein the drug layer includes a first drug layer on the first backing layer and a second drug layer on the second backing layer so that the first drug layer can be attached to the occlusal plane of upper posterior teeth and the second drug layer can be attached to the occlusal plane of lower posterior teeth at once.

2. The patch attachable to the occlusal plane of posterior teeth according to claim 1, wherein the removable part has an area at least larger than that of the backing layer and the drug layer, and has a protruding handle.

3. The patch attachable to the occlusal plane of posterior teeth according to claim 2, wherein the patch attachable to the occlusal plane of posterior teeth is a symmetric-type patch having one removable part with a protruding handle formed and two remaining parts formed at both ends of the removable part, and each of the both ends of the symmetric-type patch is equipped with a backing layer in contact with the removable part, and a drug layer in contact with the backing layer.

4. The patch attachable to the occlusal plane of posterior teeth according to claim 1, wherein the patch further comprises a wax layer in contact with the backing layer.

5. The patch attachable to the occlusal plane of posterior teeth according to claim 1, wherein the drug layer comprises a pressure-sensitive adhesive polymer.

6. The patch attachable to the occlusal plane of posterior teeth according to claim 1, wherein, after cutting the patch into 1.2 cm×5 cm and attaching 2.5 cm onto the slide glass, when the tackiness was measured with a Zwick DE/1494 universal testing machine at a speed of 5 mm/s, the drug layer has a tackiness of at least 50 gf and the backing layer has an tackiness of 10-20 gf.

7. The patch attachable to the occlusal plane of posterior teeth according to claim 4, wherein the wax layer comprises one or more wax selected from a group consisting of beeswax, carnauba wax and paraffin wax.

8. The patch attachable to the occlusal plane of posterior teeth according to claim 1, wherein a remaining part of the patch consists of the backing layer and the drug layer, and the remaining part is configured to be splitable into a plurality of pieces.

9. The patch attachable to the occlusal plane of posterior teeth according to claim 1, wherein the removable part is a PET film.

10. The patch attachable to the occlusal plane of posterior teeth according to claim 8, wherein the removable part is folded at a portion not in contact with the remaining part.

11. A method for delivering a fluorine-containing ingredient for preventing tooth decay to posterior teeth the method comprising: providing the patch attachable to the occlusal plane of posterior teeth according to claim 1, and attaching the patch to the occlusal plane of posterior teeth.

12. The method for delivering a fluorine-containing ingredient for preventing tooth decay to posterior teeth according to claim 3, wherein the removable part of the patch is removed after the patch is pressed between upper and lower teeth.

13. The patch attachable to the occlusal plane of posterior teeth according to claim 1, wherein the backing layer comprises a water-insoluble polymer, and the water-insoluble polymer is comprised in an amount of 5-15 wt % based on a total weight of the backing layer.

* * * * *